United States Patent [19]

Antonucci

[11] Patent Number: 4,536,523

[45] Date of Patent: Aug. 20, 1985

[54] DENTAL COMPOSITE FORMULATION FROM ACRYLATE MONOMER AND POLYTHIOL ACCELERATOR

[75] Inventor: Joseph M. Antonucci, Kensington, Md.

[73] Assignee: The United States of America as represented by the Secretary of the Department of Health & Human Services, Washington, D.C.

[21] Appl. No.: 565,212

[22] Filed: Dec. 23, 1983

[51] Int. Cl.$^3$ .............................................. C08L 33/08
[52] U.S. Cl. .................................. 523/115; 433/228.1
[58] Field of Search ................. 523/115; 433/202, 228

[56] References Cited

U.S. PATENT DOCUMENTS 3,991,008 11/1976 Temin et al. ........................ 523/115

Primary Examiner—Harold D. Anderson
Attorney, Agent, or Firm—Browdy and Neimark

[57] ABSTRACT

A two paste dental composite formulation is disclosed, wherein one paste comprises a polymerizable monomer and a stable organic hydroperoxide initiator, and the other paste comprises a polymerizable monomer and a polythiol accelerator, the hydroperoxide having a ten-hour half-life temperature in excess of about 100° C., and the polythiol being capable of accelerating the decomposition of the hydroperoxide into polymerization initiating free radicals at ambient temperatures.

10 Claims, No Drawings

DENTAL COMPOSITE FORMULATION FROM ACRYLATE MONOMER AND POLYTHIOL ACCELERATOR

FIELD OF THE INVENTION

The present invention relates to dentistry, especially two paste dental composite formulations, and to methods of preparing the same. More particularly, the invention relates to dental composite formulations comprising a polymerizable mixture including an initiator/accelerator system which is storage stable and which results in esthetic and color stable dental composites upon admixture of the two pastes in the absence of external heat.

BACKGROUND OF THE INVENTION

It is known that two paste dental composite formulations based on benzoyl peroxide as the polymerization initiator possess relatively poor storage stability at ambient temperatures. At temperatures higher than those usually found in clinical usage (e.g. in transport, warehouses, military or similar field situations), the relatively unstable benzoyl peroxide will decompose prematurely at a still faster rate.

Another disadvantage of the conventional two paste composites based on benzoyl peroxide is their use of the color-prone tertiary aromatic amines in the accelerator paste as the activator or promoter designed for the rapid, ambient decomposition of the benzoyl peroxide into initiating radicals.

SUMMARY OF THE INVENTION

In view of the above and other disadvantages associated with known two paste dental composite formulations, it is an object of the present invention to overcome deficiencies of the prior art, such as indicated above; to provide improvements in dentistry; and to provide a two paste composite formulation for dental restorations, fillings etc. of enhanced storage and color stability.

It is another object to provide a two paste dental composite formulation which can be polymerized at ambient temperatures so as not to lead to any inflammatory or other unfavorable responses in tissues contiguous with the composite during the polymerization thereof.

It is still another object to provide a two paste dental composite formulation which can be polymerized in a matter of a few minutes to produce a color stable polymeric composite which exhibits acceptably high tensile strength characteristics.

These and other objects and advantages are accomplished in accordance with the present invention by providing a two paste acrylate monomer-containing dental composite formulation wherein one paste includes a storage stable organic hydroperoxide initiator, and the other paste includes a polythiol material which accelerates the decomposition of the organic hydroperoxide material into initiating free radicals at ambient temperatures and which is resistant to discoloration during storage and use.

DETAILED DESCRIPTION OF EMBODIMENTS

The two paste acrylate monomer-containing dental composite formulations of the present invention may be characterized as comprising conventional polymerizable monomers, inhibitors, stabilizers, fillers and the like, in conjunction with a unique storage and color stable initiator system. The two pastes or paste-like components normally comprise the same or similar materials, except that one paste includes an organic hydroperoxide initiator and no accelerator, whereas the other paste includes a polythiol accelerator and no initiator. If desired, the initiator-containing paste may contain different and/or additional conventional components from the accelerator-containing paste, and vice versa, so long as the initiator and accelerator are maintained in separate pastes prior to mixing to form the desired composite.

The polymerizable acrylate monomers that may be used in the initiator and/or accelerator pastes of the present invention are well known in the art. See, e.g. U.S. Pat. No. 4,383,826; U.S. Pat. No. 4,333,348; and U.S. Pat. No. 3,066,112, these patents being incorporated herein by reference. Thus, some non-limiting examples of the polymerizable acrylate monomers which may be used include acrylic acid, methacrylic acid; typical alkyl methacrylates (e.g. methyl methacrylate, butyl methacrylate); cycloaliphatic methacrylates (e.g. cyclohexyl methacrylate; iso-bornyl methacrylate); aryl methacrylates (phenyl methacrylate; benzyl methacrylate; bisphenol dimethacrylates, etc.); functional methacrylates (such as 2-hydroxyethyl methacrylate; 4-methacryloxyethoxybenzaldehyde; 4-methacryloxyethoxybenzoic acid); ethylene glycol dimethacrylate; diethylene glycol dimethacrylate; triethylene glycol dimethacrylate; tetraethylene glycol dimethacrylate; polyethylene glycol and polypropylene glycol dimethacrylates; ethoxylated and propoxylated bisphenol dimethacrylates; neopentyl glycol dimethacrylate; trimethylolpropane trimethacrylate; 1,6-hexanediol-, 1,10-decanediol and 1,4-cyclohexanediol dimethacrylates; pentaerythritol tetramethacrylate; 1,10-decamethylene dimethacrylate; 1H, 1H-pentadecafluoroctyl methacrylate; 2,2-bis[p-(2'-hydroxy-3-methacryloxypropoxy)-phenyl]propane, i.e. bis-GMA; and various nonhydroxylated homologs of bis-GMA e.g. 2,2-bis[p-(2'-methacryloxyethoxy)phenyl]propane; various diurethane dimethacrylates (e.g. the diadduct of 2-hydroxyethyl methacrylate and trimethylhexamethylene diisocyanate), oligomeric urethanes with multifunctional methacrylate groups (e.g. urethane derivatives of bis-GMA and aliphatic and cycloaliphatic diisocyanates), and other prepolymer types of monomers (e.g. siloxane multifunctional methacrylates; polyfluorinated oligomeric multifunctional methacrylates, etc.) and the like. Mixtures of the above and other acrylate monomers or other copolymerizable monomers (such as any vinyl monomer capable of free radical polymerization, e.g. styrene, α-methylstyrene, vinyl biphenyl, vinyl acetate, pentafluorostyrene, and similar olefinic monomers) also may be used in either or both of the paste components. However, bulky multifunctional acrylic monomers are preferred since they have relatively low exotherms and shrinkages on polymerization, and because of their crosslinking nature, yield materials with low water sorption, high strength and excellent dimensional stability. In addition such monomers are desirable because of their low volatility and minimum potential for tissue irritation.

Either or both of the initiator-containing and accelerator-containing pastes, and generally both of them, normally also will contain a small amount of an inhibitor, such as 2,6-di-tert-butyl-p-cresol (BHT), and a particulate filler, such as finely divided silica, or glass powder. Preferably, the filler has a particle size on the order of about 200–500 mesh and has been silanized or otherwise treated with a coupling agent, such as 3-methacryloxypropyltrimethoxysilane to increase the bond strength between the filler and polymer matrix. The amount of filler that is used may vary widely depending upon the desired characteristics of the resultant composite; but generally speaking, the filler is used in an amount of from about 0% to about 90%, preferably 10% to about 90% by weight based on the weight of the total composite, and most preferably 50–90%. Suitable types of particulate fillers include silanized quartz, fused silica, crystalline silica, radiopaque fillers (e.g. barium oxide, strontium oxide, zirconium oxide, etc., containing glass fillers), synthetic minerals such as lithium aluminum silicate, organic polymeric powdered fillers (e.g. poly(methyl methacrylate); poly-(styrene); poly(tetrafluoroethylene); poly(bis-GMA), etc. Particulate fillers range in size from 0.01 to 100 microns in diameter. Appropriate coupling agents for the inorganic fillers are 3-methacryloxypropyltriethoxysilane, 3-methacryloxypropyldimethylethoxysilane and 3-methacryloxypropyldimethylchlorosilane. A mixture of various types and sizes of reinforcing fillers may be employed.

The stable organic hydroperoxide initiators that may be used in accordance with the present invention are those which exhibit a ten-hour half-life temperature on the order of at least about 100° C. Thus, hydroperoxides such as cumene hydroperoxide, which has a ten-hour half-life of 158° C., and tertiary butyl hydroperoxide may be used. Other suitable hydroperoxides include tertiary amyl hydroperoxide; p-methane hydroperoxide and 2,5-dihydroperoxy-2,5-dimethylhexane. On the contrary, conventionally used initiators, such as benzoyl peroxide, which exhibits a ten-hour half-life temperature of about 73° C., would not be suitable for use in the present formulations.

The organic hydroperoxide initiator may be present in the initiator paste in varying amounts. However, the presence of from about 0.1% to about 5% by weight based on the weight of the composite is preferred. In the presence of redox metal catalysts (e.g. cupric or ferric benzoylacetonate, cupric or ferric salicylate, cupric or ferric cyclohexanebutyrate, etc.) the concentration of hydroperoxide used is in the lower range.

The polythiol accelerators suitable for use in the present invention include those materials which contain at least two, and preferably three or more mercaptan groups which are capable of accelerating the decomposition of the organic hydroperoxide initiator at ambient temperatures, and which result in polymerized composites that exhibit superior resistance to discoloration. Thus, suitable polythiol accelerators or activators which satisfy the above criteria and therefore may be used in the present invention are multifunctional mercaptans, i.e. they contain 2 or more thiol groups (—SH) and include the following: Pentaerythritol tetra(3-mercaptopropionate); pentaerythritol tetra(thioglycolate); trimethylolethane tris(3-mercaptopropionate); trimethylolpropane tris(3-mercaptopropionate); dipentaerythritol hexa(3-mercaptopropionate); dipentaerythritol hexa(thioglycolate); polyethyeneglycol- and polypropylene glycol di-(3-mercaptopropionate)s; oligomeric and polymeric multifunctional mercaptans (e.g. poly(-methyl methacrylate) containing terminal and grafted thiol groups); various polyesters of 3-mercaptopionic acid; glycol dimercaptopropionates and the like, with pentaerythritol tetra(3-mercatopropionate) being the most preferred. The polythiol accelerator may be used in varying amounts, with amounts ranging from about 0.1 to about 10% based on the weight of the composite being typical.

In one embodiment, the amount of polythiol required to effect an ambient temperature polymerization of the composite formulation in a clinically acceptable time, e.g. from about 2 to about 8 minutes (preferably 4–8, minutes), may be reduced by the addition to the accelerator and/or initiator paste of small amounts (5–20 ppm) of a redox metal such as copper or iron, in its higher valence state, e.g., $Cu^{+2}$ or $Fe^{+3}$. The redox metal may be added to the formulation in the form of organosoluble salts such as cupric and ferric benzoylacetonates, as noted above.

The following examples are set forth for purposes of illustration only and are not intended to limit the scope of the invention. All parts and percentages are given by weight unless otherwise specified.

EXAMPLE 1

A typical two paste dental composite formulation in accordance with the present invention is set forth as follows:

| Components | Weight Percent |
| --- | --- |
| 2,2-bis[p-(3'-methacryloxy-2'-hydroxypropoxy)phenyl]propane - bis-GBMA | 13.70 |
| triethyleneglycol dimethacrylate - TEGDMA | 5.88 |
| cumene hydroperoxide - CHP | 0.4 |
| 2,6-di-tert-butyl-p-cresol - BHT | 0.02 |
| silanized glass filler (325 mesh) | 80.00 |
| ACCELERATOR PASTE | |
| bis-GMA | 12.59 |
| TEGDMA | 5.39 |
| pentaerythritol tetra (3-mercaptopropionate) - PETMP | 2.00 |
| BHT | 0.02 |
| silanized glass filler (325 mesh) | 80.00 |

Equal parts of initiator paste and accelerator paste were mixed in the conventional manner at room temperature and were allowed to set into a colorless composite. The setting time (Gilmore Needle test) was found to be 4 minutes at 37° C. and 100% relative humidity. The diametral tensile strength of the set composite (5 specimens tested), determined according to ADA Specification No. 27, was found to be 43 MPa. The color stability of the composite was tested according to ADA Specification 27, except that a Westinghouse RS bulb was substituted for the S-1 light source. The composite was found to be exceptionally color stable. The resistance to discoloration of similar composites stored in the dark for 24 hours and 7 days at 37° C.±1° C. in a 100% relative humidity chamber also was tested with favorable results.

EXAMPLE 2

The initiator paste similar to that of Example 1 was prepared, except that only 1% PETMP was used. Upon mixing equal parts of the initiator paste with an accelerator paste prepared in accordance with Example 1, a colorless composite having properties similar to those of Example 1 was formed, except that the setting time now was 7.5 minutes. Formulations with intermediate amounts of PETMP (between 1 and 2%) gave setting times intermediate between 7.5 and 4 minutes.

EXAMPLE 3

The procedure of Example 1 was repeated except that 10 ppm of ferric benzoylacetonate was added to the initiator paste. Composites having excellent esthetics and good strength (diametral tensile strength=47 MPa) were obtained upon admixture of the initiator and accelerator pastes. The setting times obtained with the 2% and 1% PETMP accelerator pastes now were 2 and 4 minutes, respectively. The color stability was excellent.

EXAMPLE 4

The procedure of Example 1 was repeated except that tertiary butyl hydroperoxide was used in place of cumene hydroperoxide. Similar results were obtained.

EXAMPLE 5

Initiator paste contains 20% bis-GMA; 5% 1,10-decamethylene dimethacrylate; 0.5% cumene hydroperoxide; 0.01% BHT and 74.5% silanized barium oxide containing glass filler. The accelerator paste has about the same monomer and glass composition: 19% bis-GMA; 5% 1,10-decamethylene dimethacrylate; 1% PETMP and 0.02% BHT with 75% of the silanized glass filler. Setting time at 37° C. is 7.5 minutes.

EXAMPLE 6

Initiator paste contains the following: 12.5% of TEGDMA; 12.5% of an oligomeric urethane multifunctional methacrylate derived from bis-GMA and 1,6-hexamethylene diisocyanate; 0.5% cumene hydroperoxide; 0.01% BHT; 74.5% silanized fused quartz. The accelerator paste has the following ingredients: The same monomer as above, plus 2% PETMP; 0.02% BHT and 73% silanized fused quartz. The setting time of a mixture of equal parts of each paste at 37° C. is 5 minutes.

EXAMPLE 7

The addition of 10 ppm of cupric benzoylacetonate to the compositions of Examples 5 and 6 reduces the setting times to 4.5 and 3.0 minutes, respectively.

EXAMPLE 8

The same as Example 1 only in this case 2% of dipentaerythritol hexa(3-mercaptopropionate) is used in the accelerator paste in place of PETMP. The setting time is 5.5 minutes.

EXAMPLE 9

Same as Example 8 except 10 ppm of cupric cyclohexanebutyrate used. Setting time at 37° C. is 2 minutes.

Initiator paste consists of 15% bis-GMA; 5% 1,6-hexamethylene dimethacrylate; 0.4% t-butyl hydroperoxide; 0.01% BHT and 79.6% of silanized barium oxide containing glass. Accelerator paste has 12.5% 1,6-hexamethylene dimethacrylate; 12.5% of an oligomeric urethane multifunctional methacrylate based on bis-GMA and 1,6-hexamethylene diisocyanate; 1% dipentaerythritol hexa(3-mercaptopropionate); 0.02% BHT and 74% silanized fused silica. Setting time of mixture of equal parts of the two is 5.5 minutes.

EXAMPLE 11

Same as Example 10 but initiator paste contains 10 ppm of ferric cyclohexanebutyrate. Setting time is 3 minutes.

Although only a limited number of specific embodiments of the present invention have been illustrated, it is, nonetheless, to be broadly construed and not limited except by the claims appended hereto. In particular, it is to be understood that the initiator/accelerator system according to this invention is useful in connection with any acrylate-type dental composition which is polymerizable by free radical initiation.

What is claimed is:

1. The reaction product of admixing two pastes of a two paste dental composite formulation, said formulation comprising: an initiator paste and an accelerator paste; said initiator paste including a first polymerizable acrylate monomer and an organic hydroperoxide initiator having a 10-hour half-life temperature in excess of about 100° C.; said accelerator paste including a second polymerizable acrylate monomer, which is the same or different from said first polymerizable acrylate monomer, and an accelerating amount of polythiol accelerator, selected from the group consisting of pentaerythritol tetra-(3-mercaptopropionate); pentaerythritol tetra-(thioglycolate); trimethylolethane tris-(3-mercaptopropionate); trimethylolpropane tris-(3-mercaptopropionate); dipentaerythritol hexa-(3-mercaptopropionate); dipentaerythritol hexa(thioglycolate); polyethyleneglycol- and polypropylene glycol di-(3-mercaptopropionate); oligomeric multi-functional mercaptans containing terminal and grafted thiol groups, polymeric multi-functional mercaptans containing terminal and grafted thiol groups; polyesters of 3-mercaptopropionic acid; glycol dimercaptopropionate; said formulation being polymerizable at ambient temperatures upon admixture of said initiator paste and said accelerator paste.

2. The product of claim 1, wherein said organic hydroperoxide initiator is selected from the group consisting of cumene hydroperoxide, tertiary-butyl hydroperoxide, tertiary amyl hydroperoxide; p-methane hydroperoxide; 2,5-dihydroperoxy-2,5-dimethylhexane and mixtures thereof.

3. The product of claim 1, wherein said initiator paste and said accelerator paste further include an inhibitor and from 0 to about 90% of a particulate inorganic filler.

4. The product of claim 3, wherein the inhibitor is 2,6-di-tert-butyl-p-cresol.

5. The reaction product of admixing two pastes of a two paste dental composite formulation, wherein said formulation comprises:
(a) an initiator paste comprising:
 (i) at least one polymerizable acrylate-containing monomer,
 (ii) from about 0.1 to about 5 weight percent of an organic hydroperoxide, based on the weight of the composite, having a ten-hour half-life temperature of at least about 100° C.,
 (iii) up to about 0.05 weight percent of an inhibitor, and
 (iv) up to about 90 weight percent of a particulate inorganic filler; and
(b) an accelerator paste comprising:
 (i) at least one polymerizable acrylate-containing monomer, (ii) from about 0.1 to about 10 weight percent of a polythiol material selected from the group consisting of pentaerythritol tetra-(3-mercaptopropionate); pentaerythritol tetra(thiolycolate); trimethylolethane tris-(3-mercaptopropionate); trimethylolpropane tris-(3-mercaptopropionate; dipentaerythritol hexa-(3-mercaptopropionate; dipentaerythritol hexa(thioglycolate); polyethylene glycol and polypropylene glycol di-(3-mercaptopropionate); oligomeric multifunctional mercaptans containing terminal and grafted thiol groups, polymeric multi-functional mercaptans containing terminal and grafted thiol groups; polyesters of 3-mercaptopropionic acid; and glycol dimercaptopropionates that will accelerate the decomposition of said organic hydroperoxide into polymerization initiating free radicale at ambient temperatures, (iii) up to about 0.05 weight percent of an inhibitor, and (iv) up to about 90 weight percent of a particulate inorganic filler.

6. The product of claim 5, wherein said organic hydroperoxide is a member selected from the group consisting of cumene hydroperoxide; tertiary butyl hydroperoxide; tertiary amyl hydroperoxide; p-methane hydroperoxide; 2,5-dihydroperoxy-2,5-dimethylhexane; and mixtures thereof.

7. The dental composite formulation of claim 6, wherein the particulate inorganic filler is a member selected from the group consisting of silica and glass.

8. The product of claim 7, wherein the inhibitor is 2,6-di-tert-butyl-p-cresol.

9. A method of forming a dental composite, comprising mixing together at ambient temperatures two paste-like components, the first of said paste-like components comprising a polymerizable acrylate-containing monomer and an organic hydroperoxide initiator having a ten-hour half-life temperature of at least about 100° C., and the second comprising a polymerizable acrylate-containing monomer and an accelerating amount of a polythiol material selected from the group consisting of pentaerythritol tetra(thioglycolate); trimethylolethane tris-(3-mercaptopropionate); trimethylolpropane tris-(3-mercaptopropionate); dipentaerythritol hexa-(3-mercaptopropionate); dipentaerythritol hexa(thioglycolate); polyethylene glycol and polypropylene glycol di-(3-mercaptopropionate); oligomeric multi-functional mercaptans containing terminal and grafted thiol groups, polymeric multifunctional mercaptans containing terminal and grafted thiol groups; polyesters of 3-mercaptopropionic acid; and glycol dimercaptopropionates, which is capable of accelerating the decomposition of said organic hydroperoxide into polymerization initiating free radicals at ambient temperatures.

10. The method of claim 7, wherein said first paste-like component further comprises an inhibitor and a particulate inorganic filler, and wherein said organic hydroperoxide is a member selected from the group consisting of cumene hydroperoxide, tertiary butylhydroperoxide, tertiary amyl hydroperoxide; p-methane hydroperoxide and 2,5-dihydroperoxy-2,5-dimethylhexane and mixtures thereof.

* * * * *